US012755832B2

(12) United States Patent
Zhang et al.

(10) Patent No.: US 12,755,832 B2
(45) Date of Patent: Oct. 6, 2026

(54) TEMPORAL INFORMATION ENHANCEMENT-BASED METHOD FOR 3D MEDICAL IMAGE SEGMENTATION

(71) Applicant: Huazhong University of science and technology, Wuhan City (CN)

(72) Inventors: Xuming Zhang, Wuhan City (CN); Mingwei Wen, Wuhan City (CN)

(73) Assignee: HUAZHONG UNIVERSITY OF SCIENCE AND TECHNOLOGY, Wuhan (CN)

( * ) Notice: Subject to any disclaimer, the term of this patent is extended or adjusted under 35 U.S.C. 154(b) by 232 days.

(21) Appl. No.: 18/634,039

(22) Filed: Apr. 12, 2024

(65) Prior Publication Data

US 2025/0140383 A1 May 1, 2025

(30) Foreign Application Priority Data

Oct. 25, 2023 (CN) ......................... 202311391101.1

(51) Int. Cl.
*G06K 9/00* (2022.01)
*G06T 7/10* (2017.01)
(Continued)

(52) U.S. Cl.
CPC ............... *G16H 30/40* (2018.01); *G06T 7/10* (2017.01); *G06T 9/00* (2013.01); *G06T 15/00* (2013.01); *G06V 10/25* (2022.01); *G06V 10/44* (2022.01)

(58) Field of Classification Search
CPC .. G06T 7/10; G06T 9/00; G06T 15/00; G06T 2207/10081; G06T 2207/10132;
(Continued)

(56) References Cited

U.S. PATENT DOCUMENTS

2021/0012504 A1* 1/2021 Myronenko .............. G06T 7/11
2021/0264589 A1* 8/2021 Jacob ...................... G06T 7/194
(Continued)

FOREIGN PATENT DOCUMENTS

CN 116664588 A * 8/2023 ............. G06V 20/64
WO WO-2020164468 A1 * 8/2020 ........... G06V 10/774

OTHER PUBLICATIONS

Transformers for 3D Medical Image Segmentation, Ali Hatamizadeh et al., CVF, 2022, pp. 574-584 (Year: 2022).*
(Continued)

*Primary Examiner* — Jayesh A Patel
(74) *Attorney, Agent, or Firm* — HSML P.C.

(57) ABSTRACT

Disclosed in the present invention is a temporal information enhancement-based method for 3D medical image segmentation, belonging to the field of medical image segmentation. The method provides a circle transformer module for extraction and fusion of temporal information, and uses temporal input to improve the training effect of a deep learning model, thereby effectively eliminating interference of similar features and blurred images. In a training phase, an input
(Continued)

sample is a temporal sequence, the model training effect is enhanced by extracting temporal information, and segmentation results before and after the combination of temporal information are both constrained, so that the model is no longer temporally dependent. In comparison with a training method in which a single sample is input, the present invention can improve the accuracy of an encoder-decoder structure-based segmentation model without costs. In an application phase, only a single frame of 3D image needs to be input, and no sequence needs to be used as an input, resulting in a more flexible application mode.

6 Claims, 2 Drawing Sheets

(51) Int. Cl.

| | |
|---|---|
| ***G06T 9/00*** | (2006.01) |
| ***G06T 15/00*** | (2011.01) |
| ***G06V 10/25*** | (2022.01) |
| ***G06V 10/44*** | (2022.01) |
| ***G16H 30/40*** | (2018.01) |

(58) Field of Classification Search

CPC . G06T 2207/20081; G06T 2207/20084; G06T 2207/30004; G06T 7/11; G06T 7/0012; G06T 17/00; G06T 2207/20104; G06T 2207/20132; G06V 10/25; G06V 10/44; G06V 10/82; G06N 3/0455; G06N 3/0895

See application file for complete search history.

(56) References Cited

U.S. PATENT DOCUMENTS

| | | | | |
|---|---|---|---|---|
| 2022/0051416 | A1 * | 2/2022 | Cao | G06T 7/0012 |
| 2025/0225776 | A1 * | 7/2025 | Zhang | G06V 10/44 |

OTHER PUBLICATIONS

Transformers in medical image segmentation: a narrative review, Rabeea Fatma Khan et al., Oct. 7, 2023, pp. 8747-8767 (Year : 2023).*

Exploring Smoothness and Class-Separation for Semi-supervised Medical Image Segmentation, Yicheng Wu et al., Springer, 2022, pp. 34-43 (Year: 2022).*

3D Medical image segmentation using parallel transformers, Qingsen Yan et al., Elsevier, 2023, pp. 1-14 (Year: 2023).*

Short-term and long-term memory self-attention network for segmentation of tumours in 3D medical images, Mingwei Wen et al., Wiley, Dec. 2022, pp. 1524-1537 (Year: 2022).*

Triple attention network for video segmentation, Yan Tian et al., Elsevier, 2020, pp. 202-211 (Year: 2020).*

End-to-End Video Instance Segmentation with Transformers, Yuqing Wang et al., CVF, 2021, pp. 8741-8750 (Year: 2021).*

Video Instance Segmentation using Inter-Frame Communication Transformers, Sukjun Hwang et al., arXiv, 2021, 1-11 (Year: 2021).*

Associating Objects with Transformers for Video Object Segmentation, Zongxin Yang et al., arXiv, 2021, pp. 1-20 (Year: 2021).*

Decoupling Features in Hierarchical Propagation for Video Object Segmentation, Zongxin Yang et al., arXiv, 2022, pp. 1-12 (Year: 2022).*

* cited by examiner

TEMPORAL INFORMATION ENHANCEMENT-BASED METHOD FOR 3D MEDICAL IMAGE SEGMENTATION

CROSS-REFERENCE TO RELATED APPLICATIONS

The present application claims priority from Chinese patent application No. 202311391101.1 filed on Oct. 25, 2023, which is incorporated herein by reference in its entirety.

TECHNICAL FIELD

The present invention belongs to the field of medical image segmentation, and more specifically, to a temporal information enhancement-based method for 3D medical image segmentation.

BACKGROUND ART

Automatic image segmentation technology is widely applied in the medical field and plays an important role in the development of computer-aided diagnosis and treatment systems such as clinical diagnosis, surgical navigation, etc. For example, puncture biopsy is the gold standard for prostate cancer diagnosis, and accurate puncture navigation techniques can effectively improve detection rates for puncture surgery and reduce trauma to patients. Real-time 3D ultrasound attracts much attention in the field of puncture navigation. Automatic segmentation of a biopsy needle in a 3D ultrasound image is the key technology to achieve navigation in puncture surgery.

Currently, many deep learning models have been proposed for image segmentation tasks, and the convolutional neural network (CNN) and the transformer have become the mainstream methods for image segmentation. In recent years, the CNN and the transformer has been combined to further improve the accuracy of segmentation networks, but the transformer module requires a lot of computing and memory resources. Therefore, the combination of the CNN and the transformer mostly depends on the encoder-decoder structure, which can eliminate redundant information by encoding so as to reduce model complexity.

With the development of image processing technology, many researchers have found that the utilization of temporal information is one of the main directions of improving the accuracy of medical image segmentation. For example, when a biopsy needle moves, temporal information can provide the reference for the relative movement and shape thereof, thereby greatly reducing the detection difficulty thereof. Thanks to the ability of the transformer to learn the global feature correlation, the transformer is very suitable for processing multi-frame images, and is widely applied to video segmentation tasks. However, the existing research mainly deals with 2D natural image sequences, and the 3D ultrasound-based method for real-time needle detection cannot achieve a good effect.

Another significant issue with medical image segmentation is the high cost of data annotation. Therefore, numerous attempts have been made to explore semi-supervised segmentation methods, which means that only a few images in a data set are annotated to achieve segmentation accuracy close to that achieved by annotating all data. A currently popular semi-supervised segmentation strategy is consistency learning, which means that the model is encouraged to have similar output when a sample or a parameter of the model is slightly disturbed. This will force output features of similar samples to be closer while output features of different categories are more different from each other, so that model performance is indirectly enhanced by using unlabeled samples. The existing consistency learning schemes are mainly implemented by setting up parallel networks or transforming input data. The former needs to occupy additional computing resources, and the performance of the latter is not ideal.

SUMMARY OF THE INVENTION

For the above defects or improvement requirements in the prior art, provided in the present invention is a temporal information enhancement-based method for 3D medical image segmentation. The method uses a circle transformer to extract motion information of a target in a 3D image sequence to perform training, thereby helping to improve segmentation accuracy for a target region image in a 3D medical image. The method is applicable to all segmentation models based on the encoder-decoder structure. Segmentation results before and after the combination of temporal information are both constrained, thereby eliminating dependency of the model on a temporal module, and improving the segmentation accuracy of the model without costs. During application, only a single frame of 3D image needs to be input, and no sequence needs to be used as an input, so that the application mode is more flexible. For unlabeled data, the method calculates a consistency loss according to output probability maps before and after the combination of temporal information, thereby facilitating improvement in model performance and requiring no additional memory.

In order to achieve the above objective, according to a first aspect of the present invention, provided is a temporal information enhancement-based method for 3D medical image segmentation, comprising:

a training phase:

performing semi-supervised training on a segmentation model by using a training set and a circle transformer module, the training set comprising a 3D medical image sequence comprising a target region, wherein part of the 3D medical image sequence, of which the gold standard of segmentation of the target region is known, is labeled data, and the rest is unlabeled data, the segmentation model comprising an encoder and a decoder, wherein the encoder is used to respectively encode each image in the 3D medical image sequence to acquire an encoded feature, and the circle transformer module is used to respectively perform processing on each image in the 3D medical image sequence as a target image to acquire a pre-decoded feature thereof, the processing comprising: performing self-attention calculation by using the encoded feature $f_s$ of the target image as K and V and by using the encoded feature $f_d$ of the other images in the 3D medical image sequence as Q, to acquire $f_m$; and performing self-attention calculation again by using $f_m$ as K and V and by using $f_s$ as Q, to acquire $f_a$, and performing layer normalization and feedforward neural network calculation on $f_a$ to acquire a pre-decoded feature $f_o$ of the target image, the decoder being used to respectively decode $f_o$ of each image to acquire a segmentation result of the image, for the labeled data, a training objective thereof being to minimize a difference between the segmentation result of each image and a label thereof, and for the unlabeled data, a training objective thereof being to minimize a difference between the segmentation result of each image and a segmentation result acquired by inputting the encoded feature of the image to the decoder.

an application phase:

inputting a 3D medical image to be segmented to the trained segmentation model to acquire a segmentation result.

According to a second aspect of the present invention, provided is a temporal information enhancement-based system for 3D medical image segmentation, comprising: a computer-readable storage medium and a processor, the computer-readable storage medium being configured to store executable instructions, and the processor being configured to read the executable instructions stored in the computer-readable storage medium, and to perform the method according to the first aspect.

According to a third aspect of the present invention, provided is a computer-readable storage medium storing computer instructions, the computer instructions being configured to cause a processor to perform the method according to the first aspect.

In general, compared with the prior art, the above technical solutions conceived by the present invention can achieve the following beneficial effects:

1. The method provided in the present invention provides a circle transformer module for extraction and fusion of temporal information, and uses temporal input to improve the training effect of a deep learning model, thereby effectively eliminating interference of similar features and blurred images. In a training phase, an input sample is a temporal sequence, the model training effect is enhanced by extracting temporal information, and segmentation results before and after the combination of temporal information are both constrained, so that the model is no longer temporally dependent. In comparison with a training method in which a single sample is input, the present invention can improve the accuracy of an encoder-decoder structure-based segmentation model without costs. In an application phase, only a single frame of 3D image needs to be input, and no sequence needs to be used as an input, resulting in a more flexible application mode.

2. According to the present invention, segmentation results before and after the combination of temporal information are both constrained by using a label, thereby improving the training effect of a segmentation model having the encoder-decoder structure without additional costs. In addition, a new consistency loss is proposed on the basis of the segmentation results before and after the combination of temporal information, thereby improving the effect of semi-supervised training of the model.

In conclusion, in the present invention, deep learning is combined with semi-supervised training of a temporal information enhancement-based segmentation model to train a 3D medical image segmentation model. During the semi-supervised training of the temporal information enhancement-based segmentation model, a circle transformer module is constructed to extract temporal motion information to optimize the training process. In addition, segmentation results before and after the combination of temporal information are both supervised, so that the model is no longer temporally dependent, thereby improving the training effect of the segmentation model without costs. A new consistency loss is proposed on the basis of the segmentation results before and after the combination of temporal information, to constrain unlabeled data to achieve semi-supervised training, thereby facilitating improvement in the model performance and requiring no additional memory.

DETAILED DESCRIPTION

In order to clarify the purpose, technical solution, and advantages of the present invention, the present invention is described in further detail below with reference to the accompanying drawings and embodiments. It should be appreciated that the specific embodiments described here are used merely to explain the present invention and are not used to limit the present invention. In addition, the technical features involved in various embodiments of the present invention described below can be combined with one another as long as they do not constitute a conflict therebetween.

Figure 1:
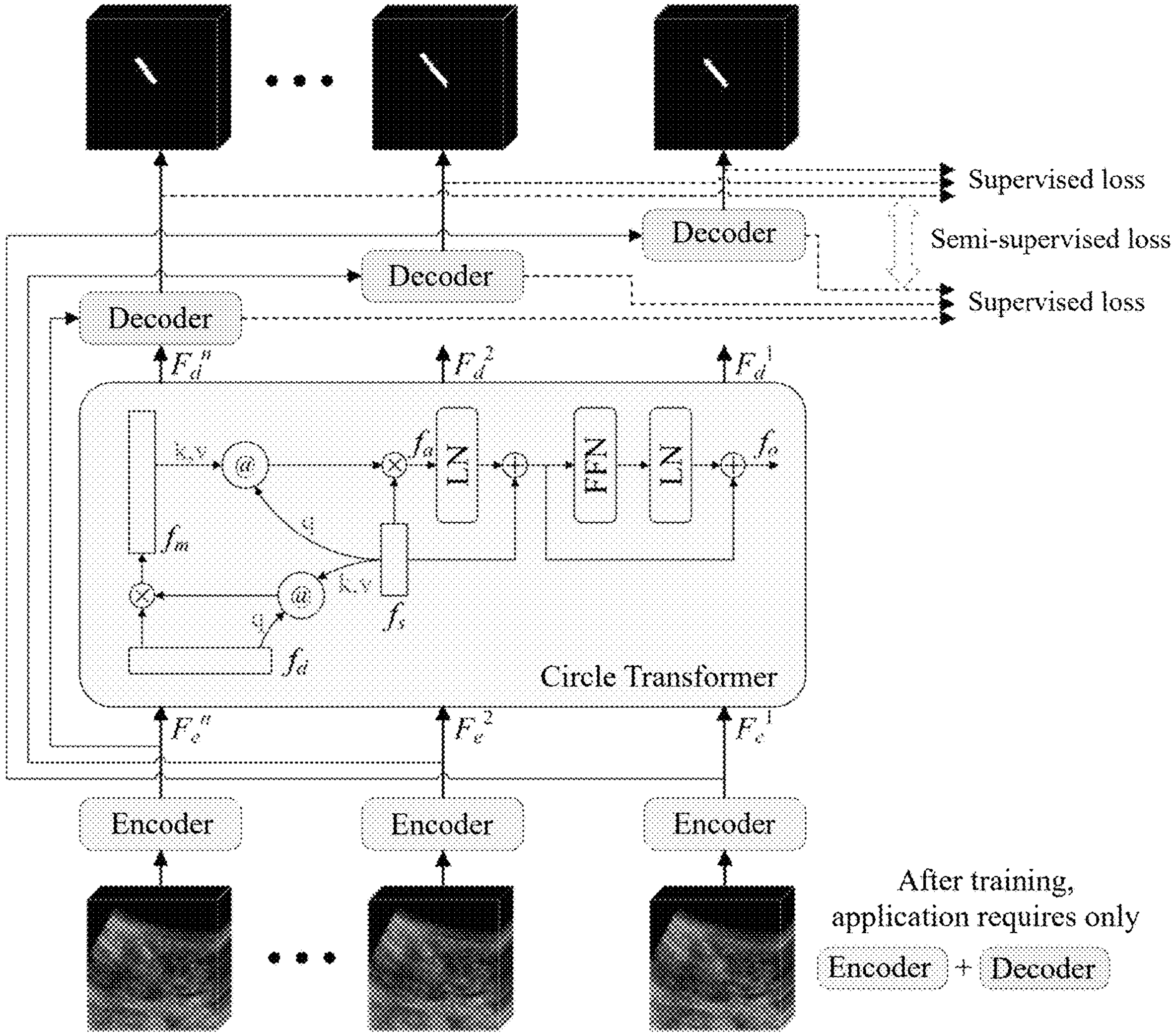
FIG. 1 is a schematic diagram of a training process of a segmentation model according to an embodiment of the present invention.

Provided in an embodiment of the present invention is a temporal information enhancement-based method for 3D medical image segmentation. The method uses a circle transformer module to extract temporal information to enhance a training effect of a segmentation model. The trained model can perform segmentation for a target region image in a medical image. As shown in FIG. 1, the method includes:

a training phase:

performing semi-supervised training on a segmentation model by using a training set and a circle transformer module, the training set including a 3D medical image sequence including a target region, wherein part of the 3D medical image sequence, of which the gold standard of segmentation of the target region is known, is labeled data, and the rest of the 3D medical image sequence, of which the gold standard of segmentation of the target region is unknown, is unlabeled data, the segmentation model including an encoder and a decoder, wherein the encoder is used to respectively encode each image in the 3D medical image sequence to acquire an encoded feature, and the circle transformer module is used to respectively perform processing on each image in the 3D medical image sequence as a target image to acquire a pre-decoded feature thereof, the processing including: performing self-attention calculation by using the encoded feature $f_s$ of the target image as K and V and by using the encoded feature $f_d$ of the other images in the 3D medical image sequence as Q, to acquire $f_m$; and performing self-attention calculation again by using $f_m$ as K and V and by using $f_s$ as Q, to acquire $f_a$, and performing layer normalization having residual connection and feedforward neural network calculation on $f_a$ to acquire a pre-decoded feature $f_o$ of the target image, the decoder being used to respectively decode $f_o$ of each image to acquire a segmentation result of the image, for the labeled data, a training objective thereof being to minimize a difference between the segmentation result of each image and a label thereof, and for the unlabeled data, a training objective thereof being to minimize a difference between the segmentation result of each image and a segmentation result acquired by inputting the encoded feature of the image to the decoder; and an application phase:

inputting a 3D medical image to be segmented to the trained segmentation model to acquire a segmentation result.

Specifically, the training phase comprises:

(1) acquiring a 3D medical image sequence including a target region, of which the gold standard of segmentation of the target region of some samples is known, cropping the original image sequence according to a region of interest, and performing pixel value normalization processing to acquire a training set sample;

(2) selecting an arbitrary mainstream deep learning segmentation model having the encoder-decoder structure, dividing the same into two parts, i.e., an encoder and a decoder, and constructing a semi-supervised training framework for a temporal information enhancement-based segmentation model, wherein in the framework, firstly, encoded features of all images in a sequence are respectively acquired by means of the encoder with shared weights, then pre-decoded features of each frame are generated from these encoded features by means of a circle transformer module in combination with temporal information, and finally, the pre-decoded features are respectively input into the decoder with shared weights to acquire a segmentation result of each frame of image, wherein in the training process, for labeled data, segmentation results acquired from the encoded feature and the pre-decoded feature are respectively supervised by means of a segmentation loss for a label thereof, and for unlabeled data, segmentation results acquired from the encoded feature and the pre-decoded feature are constrained via a consistency loss to maintain consistency therebetween; and using the training set sample acquired in step (1) and the above method to construct a semi-supervised training framework for a temporal information enhancement-based segmentation model, and performing training, so that the trained model can perform segmentation with respect to a target region included in an input image; and the application phase comprises:

for an original 3D medical image to be segmented, cropping the original image according to the region of interest, and performing a pixel value normalization operation on the cropped image to acquire a sample to be segmented; and inputting, as an input image, the sample to be segmented acquired in step (2) into the trained segmentation model acquired in step (3), thereby outputting and acquiring a segmentation result of a target region in the sample to be segmented.

The semi-supervised training framework for a temporal information enhancement-based segmentation model constructed and acquired in step (3) specifically includes:

an encoder and a decoder acquired by dividing the mainstream deep learning segmentation model having the encoder-decoder structure; and a circle transformer module, used to extract and fuse temporal information, and divided into a self-attention calculation module, a feedforward neural network (FFN), and a layer normalization module, the self-attention calculation module being used to perform two self-attention calculations, the feedforward neural network (FFN) including two fully connected layers and used to enhance non-linear expressiveness of the model, two inputs of the circle transformer module respectively representing static features and dynamic features, wherein in the training phase, when the circle transformer module processes a certain frame of image in a 3D medical image sequence, encoded features of the frame of image are expressed as the static features, and encoded features of the other frames of images in the 3D medical image sequence are expressed as the dynamic features, that is, the generated pre-decoded features of different frames correspond to different inputs. Supposing $$F_e = \{F_e^1, F_e^2, \ldots, F_e^n\} \text{ and } F_d = \{F_d^1, F_d^2, \ldots, F_d^n\}$$

respectively represent encoded features and pre-decoded features of n images. The generation of the pre-decoded features may be expressed as:

$$F_d^i = CircleT(F_e^i, F_e - \{F_e^i\}) \quad (1)$$

Regarding the structure of the circle transformer module, the circle transformer module generates the pre-decoded features by fusing two groups of features via two self-attention calculations with exchanged query objects. That is, in the first self-attention calculation, the static feature is treated as Key and Value, and the dynamic feature is treated as Query. An intermediate variable having the same size as the dynamic feature is generated by means of a weighted sum of the static features. In the second self-attention calculation, the above intermediate variable is treated as Key and Value, and the static feature is treated as Query. Layer normalization having residual connection and feedforward neural network processing are performed on a result of the second self-attention calculation, to acquire the pre-decoded feature, i.e., a final output of the circle transformer module. The final output of the circle transformer module is a twice-weighted sum of the static features. The circle transformer module performs weighted updating on the static features by means of the above calculation on the basis of correlation between the dynamic and static features under the guidance of the dynamic features while maintaining the feature size unchanged.

The method provided in the present invention utilizes the circle transformer module to introduce motion information of a target between an adjacent frame of image and a current frame of image, and enables the model to pay close attention to the shape and position features of a needle in a training process, so that the trained model has higher segmentation accuracy and is more robust in a complex environment.

During calculation of a pre-decoded feature of a certain frame of image, the static feature is denoted as $f_s$, and the dynamic feature is denoted as $f_d$, the intermediate variable of the self-attention calculation is denoted as $f_m$, the output of the self-attention calculation is denoted as $f_a$, the output of the circle transformer module is denoted as $f_o$, and LN(·) and FFN(·) respectively represent name-corresponding functions. The calculation process is as follows:

$$f_m = softmax\left(\frac{f_d \cdot f_s'}{\sqrt{C}}\right) \cdot f_s \tag{1}$$

$$f_a = softmax\left(\frac{f_s \cdot f_m'}{\sqrt{C}}\right) \cdot f_m$$

$$f_o = LN(FFN(LN(f_a) + f_a)) + LN(f_a) + f_a \tag{2}$$

The segmentation loss ($L_{seg}$) is for supervising segmentation results acquired from the encoded feature and the pre-decoded feature for a labeled sample, and consists of dice loss ($L_{Dice}$) and cross-entropy loss ($L_{CE}$). y and ŷ respectively represent a label and a prediction for a pixel i. M is the total number of pixel points in the sample. The segmentation loss is defined as follows:

$$\begin{aligned} L_{seg} &= L_{Dice} + L_{CE} \\ &= 1 - \frac{2\sum_{i=1}^{M} y_i \hat{y}_i}{\sum_{i=1}^{M} y_i + \sum_{i=1}^{M} \hat{y}_i} - [y\log(\hat{y}) + (1-y)\log(1-\hat{y})] \end{aligned} \tag{3}$$

The consistency loss ($L_{cons}$) is for unlabeled data, and maintains consistency between segmentation results acquired from the encoded feature and the pre-decoded feature. $\hat{y}_{1,i}$ and $\hat{y}_{2,i}$ respectively represent predictions for the pixel i in the segmentation results acquired from the encoded feature and the pre-decoded feature. The consistency loss is defined as follows:

$$L_{cons} = \frac{1}{M} \sum_{i=1}^{M} (\hat{y}_{1,i} - \hat{y}_{2,i})^2$$

It can be understood that the segmentation loss and the consistency loss may also be constructed according to related prior art.

Preferably in the present invention, before the semi-supervised training is performed on the segmentation model, the method further includes: cropping each image in the training set according to a region of interest, and then performing pixel value normalization processing, and before the 3D medical image to be segmented is input into the trained segmentation model, the method further includes: cropping the 3D medical image to be segmented according to the region of interest, and then performing pixel value normalization processing.

Specifically, performing cropping on the training set sample, rotating, translating, and flipping the cropped image, and performing pixel value normalization processing can reduce calculation complexity and improve diversity of training data.

Similarly, for an original 3D medical image to be segmented, the original image is cropped according to the region of interest, and a pixel value normalization operation is performed on the cropped image to acquire a sample to be segmented.

That is, the above semi-supervised training framework for a temporal information enhancement-based segmentation model may be used to train an image segmentation model having the encoder-decoder structure. The trained model is used so that the sample to be segmented acquired by an image preprocessing function module is used as a model input, and a segmentation result for a target region in the sample is output. The training utilizes the training set sample, and is performed by using the gold standard of segmentation of some samples as a label. The training set sample is acquired by acquiring a 3D medical image sequence including a target region, of which the gold standard of segmentation of the target region of some samples is known, and by cropping an original image sequence according to a region of interest, and performing pixel value normalization processing.

A medical image sequence with the total number of frames being n is used as an example. FIG. 1 is a schematic diagram showing the overall structure of a deep learning training framework according to an embodiment of the present invention, wherein a calculation process thereof is applied to training of a 3D medical image segmentation model, and an image to be segmented is input into the trained model to acquire an accurate biopsy needle region segmentation result. The specific steps may include:

(1) Encoded features of N frames of images are respectively generated by means of an encoder, and are denoted as $$F_e = \{F_e^1, F_e^2, \ldots, F_e^n\}.$$

(2) For an i-th frame of image, $$F_e^i$$

is treated as a static feature, and the other encoded features except $$F_e^i$$

are treated as dynamic features. Pre-decoded features are respectively generated by means of a circle transformer module, and are denoted as $$F_d = \{F_d^1, F_d^2, \ldots, F_d^n\}.$$

(3) Segmentation results of a target region are respectively generated from $F_e$ and $F_d$ by means of a decoder. For labeled data, the two segmentation results are respectively supervised by means of a segmentation loss according to a corresponding label. For unlabeled data, a segmentation result of a corresponding frame in the two segmentation results is constrained by means of the consistency loss.

Example 1

On the basis of the above method, an actual 3D medical image segmentation model was trained. Specifically, the following steps are included:

(1) The data set is from ultrasound-guided kidney biopsy of ten beagles. We acquired ten videos including 443 pieces of 3D volume data. Each sequence including three frames of images was extracted. Totally, 423 sequences were obtained. 393 sequences were used for training, and 30 sequences were used for testing. During training, the volume data in each sequence underwent online random data argumentation with the same parameters, including translation, scaling, flipping, and rotation.

(2) The above training set was utilized, and the SLM-SA model proposed in the training document (Short-term and long-term memory self-attention network for segmentation of tumors in 3D medical images, CAAI Transactions on Intelligence Technology, 1-14, 2023) of the training framework provided in the present invention was used. The optimal model parameters were loaded, and were applied to the test set. A segmentation result of a biopsy needle region in the image was output, and finally, quantitative evaluation was performed on the segmentation result.

Further, in order to verify the method of the present invention, the following comparative examples (the comparative examples used the same data set) were designed:

Comparative Example 1

TriANet proposed in the document (Triple attention network for video segmentation, Neurocomputing 417, 202-211, 2020) was used to implement the segmentation task of the biopsy needle region in the 3D medical image sequence. Training was performed by using the same data set, learning rate, number of iterations, and optimizer parameters as those in the method of the present invention.

Comparative Example 2

VisTR proposed in the document (End-to-end video instance segmentation with transformers, in: Proceedings of the IEEE/CVF Conference on Computer Vision and Pattern Recognition, 8737-8746, 2021) was used to implement the segmentation task of the biopsy needle region in the 3D medical image sequence. Training was performed by using the same data set, learning rate, number of iterations, and optimizer parameters as those in the method of the present invention.

Comparative Example 3

IFC proposed in the document (Video instance segmentation using inter-frame communication transformers, in: Proceedings of the 35th Conference on Neural Information Processing Systems, 2021) was used to implement the segmentation task of the biopsy needle region in the 3D medical image sequence. Training was performed by using the same data set, learning rate, number of iterations, and optimizer parameters as those in the method of the present invention.

Comparative Example 4

AOT proposed in the document (Associating objects with transformers for video object segmentation, in: Proceedings of the 35th Conference on Neural Information Processing Systems, 2021) was used to implement the segmentation task of the biopsy needle region in the 3D medical image sequence. Training was performed by using the same data set, learning rate, number of iterations, and optimizer parameters as those in the method of the present invention.

Comparative Example 5

DeAOT proposed in the document (Decoupling features in hierarchical propagation for video object segmentation, in: Proceedings of the 35th Conference on Neural Information Processing Systems, 2022) was used to implement the segmentation task of the biopsy needle region in the 3D medical image sequence. Training was performed by using the same data set, learning rate, number of iterations, and optimizer parameters as those in the method of the present invention.

Result Analysis:

To show the advantages of the present invention, the segmentation effect of Example 1 was compared with those of Comparative Examples 1-5. In quantitative comparison, the dice coefficient, the needle tip positioning error ($E_{tip}$), the needle length error ($E_{len}$), and the needle angle error ($E_{ang}$) were used for evaluation. The DSC was defined as follows:

$$DSC = \frac{2 \cdot TP}{(TP + FP) + (TP + FN)} \tag{13}$$

where TP, FP, and FN respectively represented the number of true positives, the number of false positives, and the number of false negatives in the predicted pixel classification results in comparison to the gold standard. For $E_{tip}$, $E_{len}$, and $E_{ang}$, respective needle tip positions, lengths, and angles were extracted from the segmentation results and labels by means of a linear fitting algorithm, and then the mean square error (MSE) of each parameter was calculated.

Table 1 lists four quantitative evaluation metrics of the segmentation results of Example 1 and Comparative Examples 1-5, and the running speed and parameters. As can be seen from the table, in Example 1 compared with Comparative Examples 1-5, the four quantitative evaluation metrics DSC, $E_{tip}$, $E_{len}$, and $$E_{ang}^{z}$$

are obviously improved. In addition, the parameters in Example 1 are only 0.87 M, and the computation speed reaches 55 frames/second (FPS), thereby achieving real-time segmentation for a biopsy needle in a 3D ultrasound image more quickly and accurately.

TABLE 1

Segmentation accuracy, speed, and parameters of each segmentation method for a selected data set

| Methods | DSC ↑ | $E_{tip}$ ↓ | $E_{len}$ ↓ | $E_{ang}^x$ ↓ | $E_{ang}^y$ ↓ | $E_{ang}^z$ ↓ | FPS ↑ | Parameters ↓ |
|---|---|---|---|---|---|---|---|---|
| Ours | 0.771 | 1.28 | 1.78 | 2.57 | 3.38 | 0.58 | 55 | 0.87M |
| TriANet | 0.746 | 1.87 | 2.20 | 2.70 | 3.89 | 0.65 | 4 | 89.44M |
| VisTR | 0.693 | 2.79 | 4.49 | 3.03 | 3.79 | 1.76 | 42 | 72.38M |
| IFC | 0.721 | 2.40 | 4.98 | 2.54 | 3.09 | 0.97 | 75 | 55.98M |
| AOT | 0.719 | 2.22 | 3.62 | 2.26 | 2.77 | 0.71 | 15 | 61.80M |
| DeAOT | 0.765 | 1.91 | 2.19 | 2.17 | 2.80 | 0.76 | 33 | 66.48M |

Figure 2:
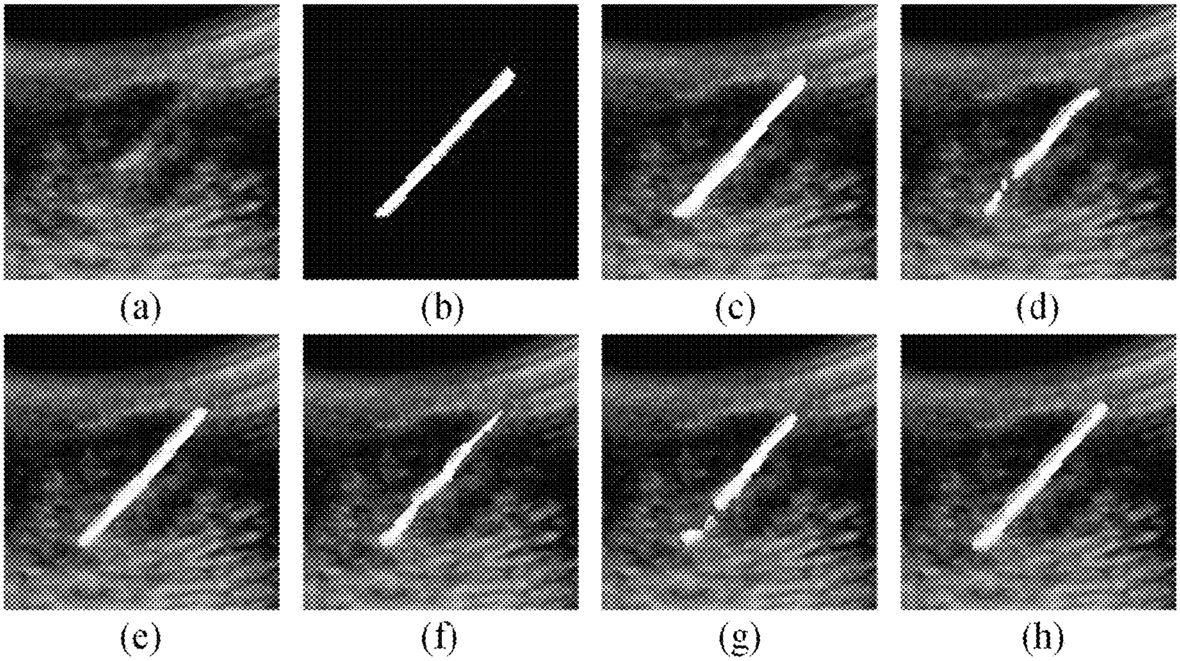
FIG. 2 is visual effect diagrams of segmented images corresponding to Example 1 and Comparative Examples 1-5, and (a) to (h) in FIG. 2 sequentially correspond to: an original image, a label, a visual effect diagram after processing in Example 1, a visual effect diagram after processing in Comparative Example 1, a visual effect diagram after processing in Comparative Example 2, a visual effect diagram after processing in Comparative Example 3, a visual effect diagram after processing in Comparative Example 4, and a visual effect diagram after processing in Comparative Example 5.

In order to more intuitively show the advantages of the present invention, visual effect diagrams of segmented images corresponding to Example 1 and Comparative Examples 1-5 are provided. As shown in (a) to (h) in FIG. 2, (a) and (b) show the original medical image and a real label corresponding thereto. (c) to (h) are respectively segmentation results acquired by our method and TriANet, VisTR, IFC, AOT, and DeAOT models, where the white, light gray, and dark gray regions respectively represent the true positive, false positive, and false negative regions in the biopsy needle detection results. Obviously, the biopsy needle length, the needle tip position, and the needle angle measured by our method are well consistent with gold standards thereof.

The above embodiment in which needle detection is used as an example sufficiently shows that the present invention facilitates improvement in detection accuracy of a biopsy needle in a 3D medical image. The method and system are based on deep learning, can be used to train an encoder-decoder structure-based segmentation model, and in particular can be used for a segmentation task for a biopsy needle region of a 3D medical image.

The above embodiment is merely an example. In addition to the biopsy needle, the method and system of the present invention may also be used to perform segmentation on 3D medical images having other target regions such as surgical instruments, organs, etc., that move over time.

Provided in an embodiment of the present invention is a temporal information enhancement-based system for 3D medical image segmentation, including: a computer-readable storage medium and a processor,

- the computer-readable storage medium being configured to store executable instructions, and
- the processor being configured to read the executable instructions stored in the computer-readable storage medium, and to perform the method according to any one of the above embodiments.

Provided in an embodiment of the present invention is a computer-readable storage medium storing computer instructions, the computer instructions being configured to cause a processor to perform the method according to any one of the above embodiments.

It can be easily understood by a person skilled in the art that the foregoing description is only preferred embodiments of the present invention and is not intended to limit the present invention. Any modifications, identical replacements, improvements and so on that are within the spirit and principle of the present invention should be included in the scope of protection of the present invention.

The invention claimed is:

1. A temporal information enhancement-based method for 3D medical image segmentation, comprising:

a training phase:

performing semi-supervised training on a segmentation model by using a training set and a circle transformer module, the training set comprising a 3D medical image sequence comprising a target region, wherein part of the 3D medical image sequence is labeled data, and the rest is unlabeled data, the segmentation model comprising an encoder and a decoder, wherein the encoder is used to respectively encode each image in the 3D medical image sequence to acquire an encoded feature, and the circle transformer module is used to respectively perform processing on each image in the 3D medical image sequence as a target image to acquire a pre-decoded feature thereof, the processing comprising: performing self-attention calculation by using the encoded feature $f_s$ of the target image as K and V and by using the encoded feature $f_d$ of the other images in the 3D medical image sequence as Q, to acquire $f_m$; and performing self-attention calculation again by using $f_m$ as K and V and by using $f_s$ as Q, to acquire $f_a$, and performing layer normalization and feedforward neural network calculation on $f_a$ to acquire a pre-decoded feature $f_o$ of the target image, the decoder being used to respectively decode $f_o$ of each image to acquire a segmentation result of the image, for the labeled data, a training objective thereof being to minimize a difference between the segmentation result of each image and a label thereof, and for the unlabeled data, a training objective thereof being to minimize a difference between the segmentation result of each image and a segmentation result acquired by inputting the encoded feature of the image to the decoder, and an application phase:

inputting a 3D medical image to be segmented to the trained segmentation model to acquire a segmentation result.

2. The method according to claim 1, wherein $$f_m = softmax\left(\frac{f_d \cdot f_s'}{\sqrt{C}}\right) \cdot f_s$$

$$f_a = softmax\left(\frac{f_s \cdot f_m'}{\sqrt{C}}\right) \cdot f_m$$

$$f_o = LN(FFN(LN(f_a) + f_a)) + LN(f_a) + f_a$$

wherein LN(·) and FFN(·) respectively represent name-corresponding functions, $$f_s'$$

and $$f_m'$$

are respectively transposed matrices of $f_s$ and $f_m$, and C is the length of a feature vector set in the segmentation model.

3. The method according to claim 1, wherein before the semi-supervised training is performed on the segmentation model, the method further comprises: cropping each image in the training set according to a region of interest, and then performing pixel value normalization processing, and before the 3D medical image to be segmented is input into the trained segmentation model, the method further comprises: cropping the 3D medical image to be segmented according to the region of interest, and then performing pixel value normalization processing.

4. The method according to claim 1, wherein a loss of the training phase comprises a segmentation loss $L_{seg}$ for the labeled data and a consistency loss $L_{cons}$ for the unlabeled data.

5. The method according to claim 4, wherein $$L_{seg} = L_{Dice} + L_{CE} = 1 - \frac{2\sum_{i=1}^{M} y_i \hat{y}_i}{\sum_{i=1}^{M} y_i + \sum_{i=1}^{M} \hat{y}_i} - [y\log(\hat{y}) + (1-y)\log(1-\hat{y})],$$

$$L_{cons} = \frac{1}{M}\sum_{i=1}^{M} (y_i - \hat{y}_i)^2,$$

wherein $L_{Dice}$ is a dice loss, and $L_{CE}$ is a cross-entropy loss, y and ŷ respectively represent a label and a prediction for a pixel i in a segmentation result acquired from the pre-decoded feature, $\hat{y}_{1,i}$ and $\hat{y}_{2,i}$ respectively represent predictions for the pixel i in the segmentation results acquired from the encoded feature and the pre-decoded feature, and Mis the total number of pixel points of the image.

6. A temporal information enhancement-based system for 3D medical image segmentation, comprising: a computer-readable storage medium and a processor, the computer-readable storage medium being configured to store executable instructions, and the processor being configured to read the executable instructions stored in the computer-readable storage medium, and to perform the method according to claim 1.

* * * * *